(12) United States Patent
Tillotson

(10) Patent No.: US 10,161,905 B2
(45) Date of Patent: Dec. 25, 2018

(54) SMOKE DETECTOR HAVING A MAGNET

(71) Applicant: The Boeing Company, Chicago, IL (US)

(72) Inventor: Brian Tillotson, Seattle, WA (US)

(73) Assignee: The Boeing Company, Chicago, IL (US)

( * ) Notice: Subject to any disclaimer, the term of this patent is extended or adjusted under 35 U.S.C. 154(b) by 6 days.

(21) Appl. No.: 15/599,566

(22) Filed: May 19, 2017

(65) Prior Publication Data

US 2018/0335402 A1 Nov. 22, 2018

(51) Int. Cl.
*G01N 27/66* (2006.01)
*G01T 7/12* (2006.01)
*G08B 17/113* (2006.01)

(52) U.S. Cl.
CPC ............. *G01N 27/66* (2013.01); *G01T 7/125* (2013.01); *G08B 17/113* (2013.01)

(58) Field of Classification Search
CPC ........ G01N 27/66; G01T 7/125; G08B 17/113
See application file for complete search history.

(56) References Cited

U.S. PATENT DOCUMENTS 3,913,082 A * 10/1975 Hamm .................. G08B 17/11
250/381
4,456,907 A * 6/1984 Johnson ............... G08B 29/145
250/381

\* cited by examiner

*Primary Examiner* — Hugh H Maupin
(74) *Attorney, Agent, or Firm* — McDonnell Boehnen Hulbert & Berghoff LLP

(57) ABSTRACT

An example smoke detector includes (i) a chamber; (ii) a first electrode disposed within the chamber; (iii) a second electrode disposed within the chamber, wherein gas is disposed in an inner space of the chamber between the first electrode and the second electrode; (iv) a radioactive source generating alpha particles within inner space of the chamber; and (v) a magnet coupled to the chamber, where the magnet generates a magnetic field in the inner space of the chamber.

20 Claims, 4 Drawing Sheets

SMOKE DETECTOR HAVING A MAGNET

FIELD

The present disclosure relates generally to smoke detectors.

BACKGROUND

A smoke detector is a device that senses the presence of smoke, typically as an indicator of fire. Commercial security devices issue a signal to a fire alarm control panel as part of a fire alarm system, while household smoke detectors, also known as smoke alarms, generally issue a local audible or visual alarm from the detector itself.

Smoke detectors may be housed in plastic enclosures, typically shaped like a disk about 150 millimeters (6 in) in diameter and 25 millimeters (1 in) thick, but shape and size vary. Smoke can be detected either optically (photoelectric) or by physical process (ionization), Detectors may use either, or both, methods.

Smoke detectors in large commercial, industrial, and residential buildings are usually powered by a central fire alarm system, which is powered by the building power with a battery backup. Domestic smoke detectors range from individual battery-powered units, to several interlinked mains-powered units with battery backup; if any unit detects smoke, all trigger even in the absence of electricity.

An ionization smoke detector uses a radioisotope to ionize air or any other gas within a chamber, and an electric current is generated via the ions created within the chamber. If smoke enters the chambers, the electric current changes. A difference in the electric current is detected and an alarm is generated.

The radioisotope in ionizing smoke detectors may pose a potential environmental hazard, if the smoke detector is damaged (e.g., in a fire), thus causing the radioisotope to be exposed. Exposure of radioactive material to the environment may pose environmental and health risks. It may thus be desirable to have systems, apparatuses, and smoke detectors that use a reduced amount of radioactive material, yet have enhanced efficiency to maintain sensitivity to smoke. This way, the environmental risk may be reduced.

SUMMARY

The present disclosure describes embodiments that relate to a smoke detector having a magnet.

In one aspect, the present disclosure describes a smoke detector. The smoke detector includes: (i) a chamber; (ii) a first electrode disposed within the chamber; (iii) a second electrode disposed within the chamber, where gas is disposed in an inner space of the chamber between the first electrode and the second electrode; (iv) a radioactive source generating alpha particles within inner space of the chamber; and (v) a magnet coupled to the chamber, where the magnet generates a magnetic field in the inner space of the chamber.

In another aspect, the present disclosure describes another smoke detector. The smoke detector includes: (i) a chamber; (ii) a first electrode disposed within the chamber; (iii) a second electrode disposed within the chamber, where air is disposed within the chamber between the first electrode and the second electrode; (iv) a radioactive source emitting alpha particles in the air between the first electrode and the second electrode; and (v) a magnet coupled to the chamber, where the magnet generates a magnetic field having magnetic flux lines passing through the air between the first electrode and the second electrode, and the magnet is oriented such that at least a portion of the magnetic flux lines is substantially parallel to a longitudinal axis of the chamber.

In still another aspect, the present disclosure describes another smoke detector. The smoke detector includes: (i) a chamber; (ii) a first electrode disposed within the chamber; (iii) a second electrode disposed within the chamber, where air is disposed between the first electrode and the second electrode; (iv) a radioactive source emitting alpha particles in the air between the first electrode and the second electrode; (v) a first magnet mounted to an exterior surface of the chamber at a first side of the chamber; and (vi) a second magnet mounted to the exterior surface of the chamber at a second side of the chamber opposite the first side thereof, where the first magnet and the second magnet cooperate to generate a magnetic field having magnetic flux lines passing through the air disposed between the first electrode and the second electrode.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying Figures.

DETAILED DESCRIPTION

Figure 1:
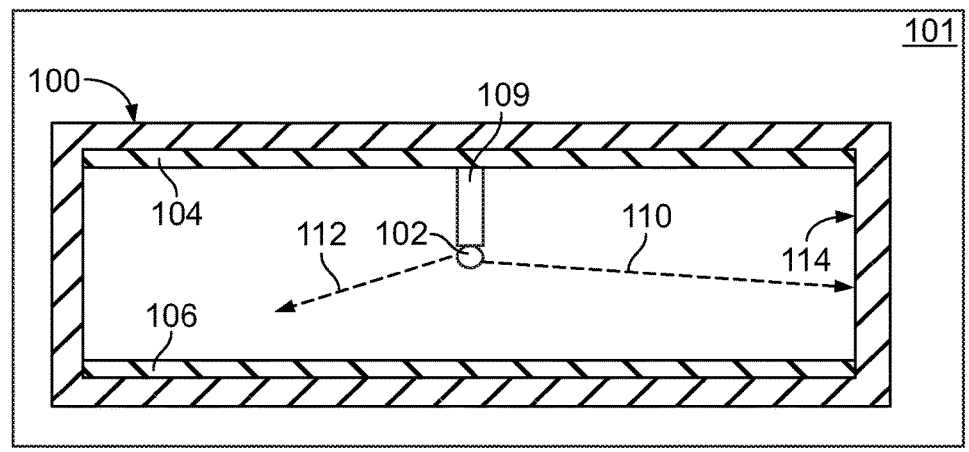
FIG. 1 illustrates a cross section of an ionization chamber of a smoke detector, in accordance with an example implementation.
Figure 2:
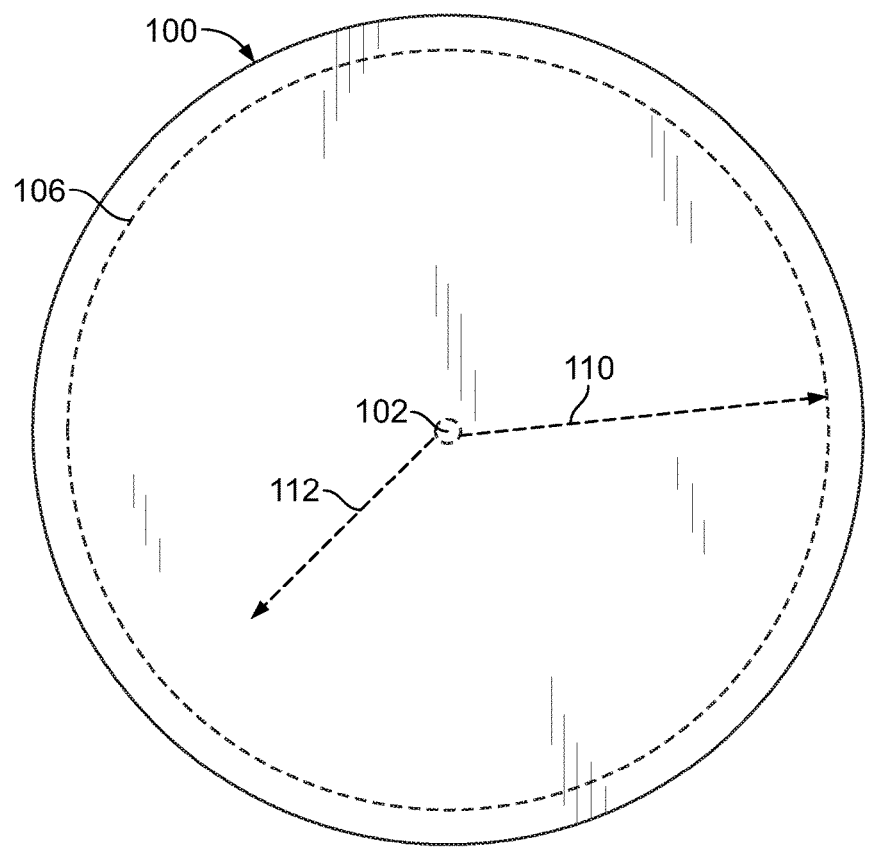
FIG. 2 illustrates a bottom view of the ionization chamber shown in FIG. 1, in accordance with an example implementation.

FIG. 1 illustrates a cross section of an ionization chamber 100 of a smoke detector 101, and FIG. 2 illustrates a bottom view of the ionization chamber 100, in accordance with an example implementation. The smoke detector 101 is not shown in FIG. 2 to reduce visual clutter in the drawing.

In examples, the ionization chamber 100 may have a cylindrical shape. However, other shapes are possible. The ionization chamber 100 includes a radioactive source 102 that emits alpha particles in an inner space of the ionization chamber 100. As an example, the radioactive source 102 may include a radioisotope such as americium-241 configured to emit alpha particles within the ionization chamber 100. For instance, the radioactive source 102 may include a small amount of americium-241, e.g., 0.29 microgram (μg). The radioactive element americium has a half-life of 432 years, and is a source of alpha particles with a kinetic energy of about 5 million electron-volts (MeV).

The ionization chamber 100 also includes a first electrode 104 and a second electrode 106. A battery or some other power source can be used to create a voltage or potential difference between the electrode 104 and the electrode 106. As a result, one of the electrodes, e.g., the electrode 104, may have a positive voltage, whereas the other electrode, e.g., the electrode 106, may have a negative voltage.

As shown in FIG. 2, if the ionization chamber 100 is shaped as a cylinder, the electrodes 104 and 106 may be shaped as disks disposed within the ionization chamber 100. In this example, the first electrode 104 may be disposed at or mounted to an interior surface of a first base of the cylindrically shaped ionization chamber 100, whereas the second electrode 106 may be disposed at or mounted to an interior surface of a second base opposite the first base of the cylindrically shaped ionization chamber 100.

The alpha particles generated by the radioactive source 102 in the inner space of the ionization chamber 100 ionize the oxygen and nitrogen atoms of the air or other gas disposed between the electrodes 104 and 106. Ionization of an oxygen or nitrogen atom "knocks" an electron off of the atom. As a result, a free electron (with a negative charge) is generated and the atom is left missing one electron, and therefore the atom turns into an ion having a positive charge. The negative electron is attracted to the electrode with a positive voltage (e.g., the electrode 104), and the positively charged ion is attracted to the electrode a negative voltage (e.g., the electrode 106), and an electric current is thus generated.

The smoke detector 101 may include an electronic circuit that detects the small amount of electrical current that the electrons and ions moving toward the electrodes 104 and 106 generate. The ionization chamber 100 is not sealed and is configured to allow smoke to enter therein. When smoke enters the ionization chamber 100, the smoke disrupts the electric current. Particularly, the smoke particles attach to the ions and neutralize them, and therefore the ions would not be available to carry the electric current in the ionization chamber 100.

The electronic circuit of the smoke detectors 101 may thus sense a drop in electric current between the electrodes 104 and 106 and sets off an alarm. For example, the smoke detector 101 may include a second chamber (not shown) therein. The second chamber may be similar to the ionization chamber 100, but is sealed and operates as a reference chamber. The radioactive source 102 or a similar source may also emit alpha particles within the second chamber, which may include electrodes similar to the electrodes 104 and 106, and thus an electric current is generated therein as well. Because the second chamber is sealed, smoke might not enter therein, and the electric current in the second chamber would not be disrupted or dropped as a result of smoke. The electronic circuit of the smoke detector 101 may detect a difference in the electric current of the ionization chamber 100 and the respective electric current of the second chamber, and accordingly sound an alarm.

In another example, the smoke detector 101 may include a Metal Oxide Semiconductor Field Effect Transistor (MOSFET). The battery of the smoke detector 101 may bias the gate of the MOSFET so as to generate an electric current through the MOSFET. However, the electric current generated as a result of ionization of air molecules within the ionization chamber 100, opposes and cancels the electric current from the battery through the MOSFET. If smoke enters the ionization chamber 100, the electric current generated via the ions therein is disrupted and does not cancel the electric current from the battery. As a result, electric current flows through the MOSFET, thereby triggering an alarm. Other example detection techniques are also available.

The amount of radioactive material in the radioactive source 102 (e.g., 0.29 μg of americium 241) is an amount that provides sufficient ionization electric current to detect smoke, while producing a low level of radiation outside the smoke detector 101. However, the radioactive material might pose a potential environmental hazard when the smoke detector 101 is disposed of, or if the smoke detector 101 is damaged and the radioactive material is exposed. Therefore, it may be desirable to reduce the amount of radioactive material used in the radioactive source 102. Disclosed herein are systems, apparatuses, ionization chambers, and smoke detectors that achieve an enhanced efficiency of ionization within the ionization chamber 100 so as to provide the same smoke detection ability and safety level, while using a reduced amount of radioactive material.

As mentioned above, the radioactive source 102 is chosen to emit alpha particles. Alpha particles are used as opposed to beta (electron) and gamma (electromagnetic) radiation because alpha particles have high ionization rates. As such, sufficient air particles will be ionized and a detectable electric current is generated. Further, alpha particles have low penetrative power. Thus, many alpha particles might be stopped by the plastic of a body or container of the smoke detector 101. However, some alpha particles might escape the smoke detector 101.

In examples, the radioactive material in the radioactive source 102 may be configured as thin layers or tiny particles. This configuration may ensure that the radioactive material absorbs or slows relatively few alpha particles emitted from within the radioactive material.

Further, in examples, the radioactive source 102 may be positioned at the center of the ionization chamber 100 between the two electrodes 104 and 106. For instance, the radioactive source 102 may be mounted to a post or pole 109. As an example, the radioactive source 102 may be coupled to a tip of the pole 109. The pole 109 protrudes from the electrode 104 or 106 within the inner space of the ionization chamber 100 so as to position the radioactive source 102 proximate to, or substantially at, a center of the ionization chamber 100. The term "substantially at the center" or "proximate to the center" indicates that the radioactive source 102 is placed within a threshold distance, such as 5 millimeter, from the center of the ionization chamber 100. With this configuration, an alpha particle emitted in any direction between the electrodes 104 and 106 ionizes air molecules disposed therebetween. However, in other examples, the radioactive source 102 might be positioned closer to one of the electrodes 104, 106.

As depicted schematically in FIGS. 1 and 2, when alpha particles are emitted, they may traverse straight line paths such as paths 110 and 112. Due to geometry of the ionization chamber 100 and the geometry of the radioactive source 102, some particles may travel longer paths compared to other particles. For example, a particle emitted from deeper within the chunk of radioactive material of the radioactive source 102 may lose more energy before it exits the radioactive source 102 than one emitted from close to the surface of the radioactive source 102. The alpha particle emitted from deeper inside therefore travels less distance in air before stopping, even if it does not encounter an electrode or chamber wall. Regarding the geometry of the ionization chamber 100, for example, some alpha particles may traverse a longer path, e.g., the path 110, between the radioactive source 102 and an interior peripheral side surface 114 of the ionization chamber 100. Other alpha particles may traverse a shorter path, e.g., the path 112, between the radioactive source 102 and the electrodes 104, 106.

Alpha particles traversing longer paths within the ionization chamber 100 may be more effective in ionizing air particles than alpha particles traversing a shorter path because particles traversing through the longer paths spend more time expending their energy within the ionization chamber 100. Once an alpha particle reaches the interior surface 114 of the ionization chamber 100 or one of the electrodes 104, 106, the alpha particle may impart its remaining energy to molecules of the interior surface 114 or the electrodes 104, 106. Such imparted energy is wasted as it is not used to ionize air molecules in the ionization chamber 100. Thus, the energy spent within the ionization chamber 100 is used to ionize the air particles therein, while the energy spent at the interior surface 114 or electrodes 104, 106 is wasted.

Further, an alpha particle is characterized in that, as it travels through the air within the ionization chamber 100, the energy lost by the alpha particle and used to ionize air molecules is inversely proportional to the square of its velocity. Thus, a peak of energy loss occurs just before the alpha particle comes to a complete stop. This peak is referred to as the Bragg peak.

Figure 3:
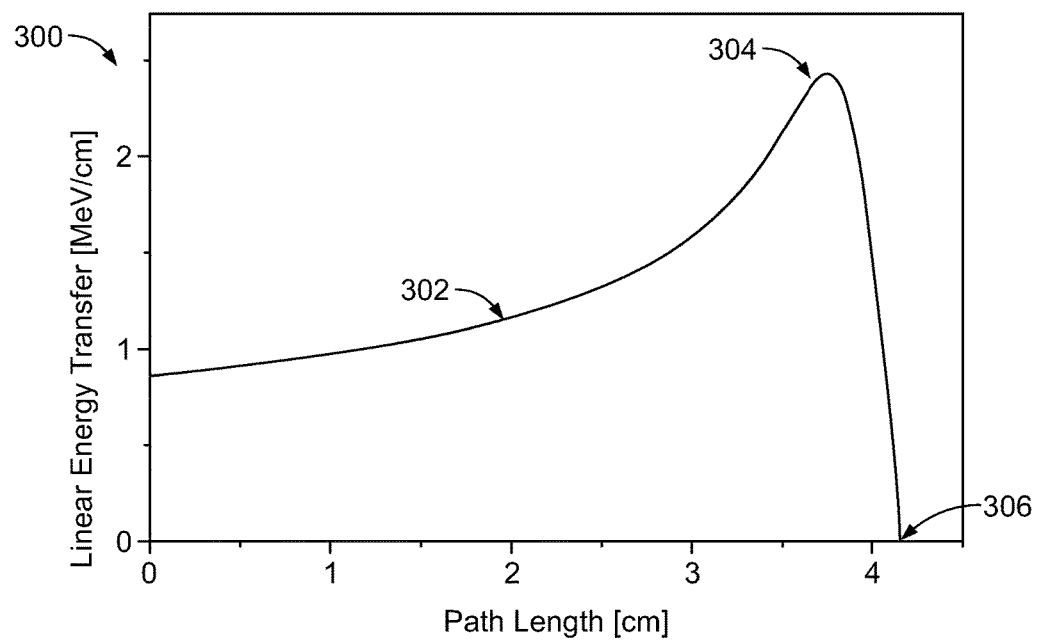
FIG. 3 illustrates a graph showing variation of linear energy transfer of an alpha particle as the alpha particle travels through air, in accordance with an example implementation.

FIG. 3 illustrates a graph 300 showing variation of linear energy transfer of an alpha particle as the alpha particle travels through air, in accordance with an example implementation. The vertical axis of the graph 300 represents the linear energy transfer, which is the kinetic energy imparted from the alpha particle to air molecules, mostly by ionization, in Million electron-volt per centimeter traveled (MeV/cm). The horizontal axis represents path length of the alpha particle in (cm). The curve 302 may be referred to as the Bragg curve and illustrates the variation of the linear energy transfer of the alpha particle with path length.

A peak 304 of the curve 302 occurs before the alpha particle stops at point 306. Thus, the majority of the energy of the alpha particle is spent right before its stops. As such, most of the energy of the alpha particle may be spent when, or right before, it impacts the interior surface 114 or the electrode 104 or 106 within the ionization chamber 100. With this configuration, a large amount of the energy of the alpha particles might be wasted, and not utilized to ionize air molecules.

In some examples, some alpha particles may escape the ionization chamber 100. In an example, if an alpha particle escapes the ionization chamber 100 with 10% of its path length before stoppage still remaining, then due to the shape of the curve 302, as much as 40% of the ions created by the alpha particle would be generated outside the ionization chamber 100.

As a result, the radioactive material of the radioactive source 102 is sized while taking into consideration that in many cases most of the energy of the alpha particles is wasted and not used to ionize the air within the ionization chamber 100. If the alpha particles are forced to stay longer or stop within the ionization chamber 100 before impacting the interior surface 114 or the electrode 104 or 106, most of the energy of the alpha particles would be used to ionize air molecules within the ionization chamber 100. In this case, efficiency of the smoke detector may be enhanced, and thus less radioactive material might be used to achieve the same smoke detection capability of the smoke detector 101. Also, a smaller ionization chamber 100 may be used to achieve the same smoke detection capability.

Figure 4:
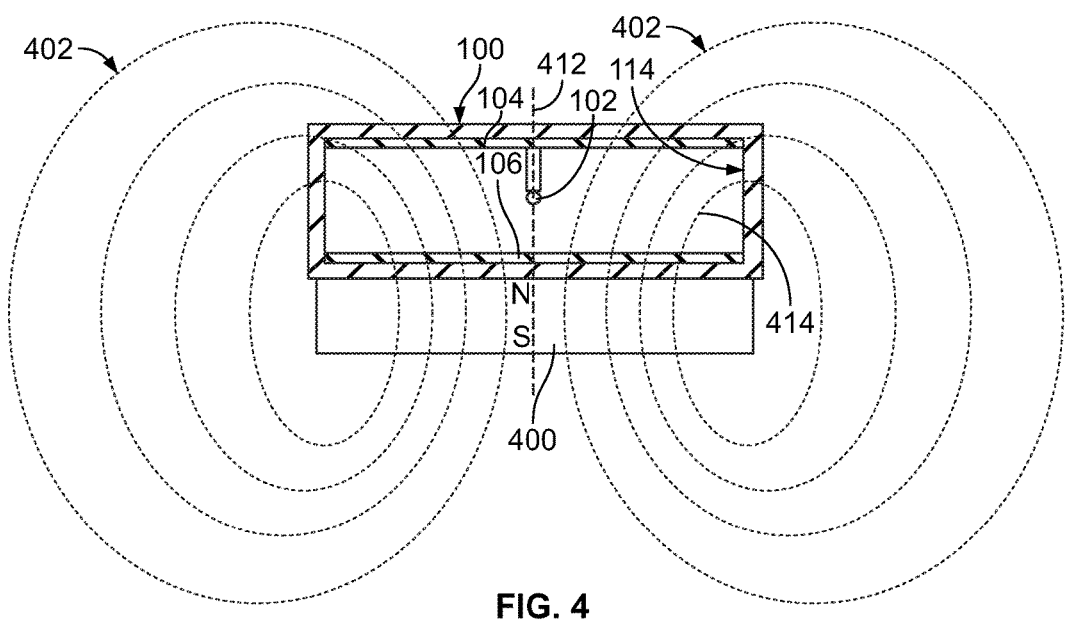
FIG. 4 illustrates a magnet coupled to an ionization chamber, in accordance with an example implementation.

FIG. 4 illustrates a magnet 400 coupled to the ionization chamber 100, in accordance with an example implementation. In examples, the magnet 400 may be coupled or mounted to an exterior surface of the ionization chamber 100. For example, if the ionization chamber 100 is cylindrical, the magnet 400 may be coupled to an exterior surface of one of the bases of the ionization chamber 100. As shown in FIG. 4, the magnet 400 may be coupled, for example, to a side of the ionization chamber 100 that is adjacent to the electrode 106. The magnet 400 may be disposed parallel to the electrode 106.

However, in other examples, the magnet 400 could be coupled to the ionization chamber 100 adjacent to the electrode 104. In an example, the magnet 400 may be mounted within the ionization chamber 100. In some examples, the magnet might not be parallel to the electrode 104 or 106. Further, the magnet 400 is disposed within the smoke detector 101, which is not shown in FIG. 4 to reduce visual clutter in the drawing.

The magnet 400 generates a magnetic field 402 having magnetic flux lines passing through the air within the ionization chamber 100. Because the alpha particles emitted by the radioactive source 102 are positively charged, the magnetic field 402 causes paths of the alpha particles to curve within the ionization chamber 100.

Figure 5:
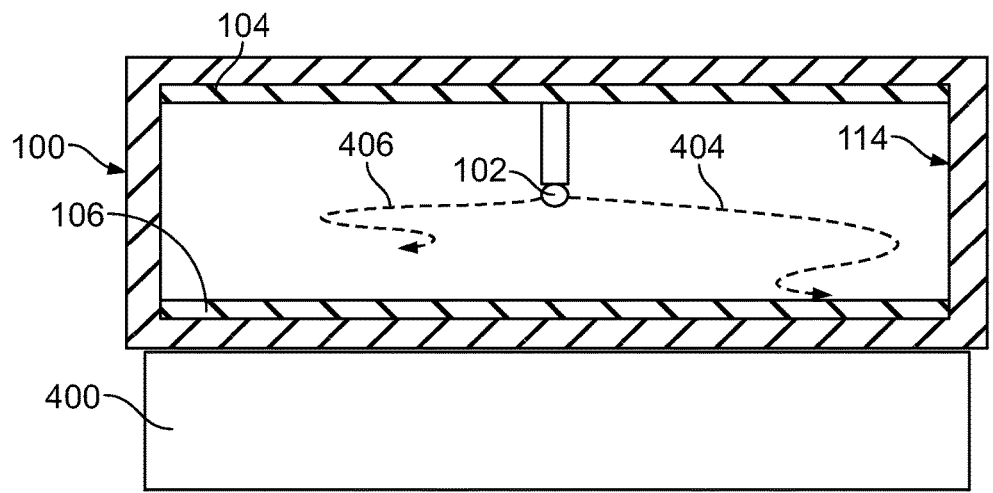
FIG. 5 illustrates a cross section of an ionization chamber schematically showing curved paths of alpha particles, in accordance with an example implementation.
Figure 6:
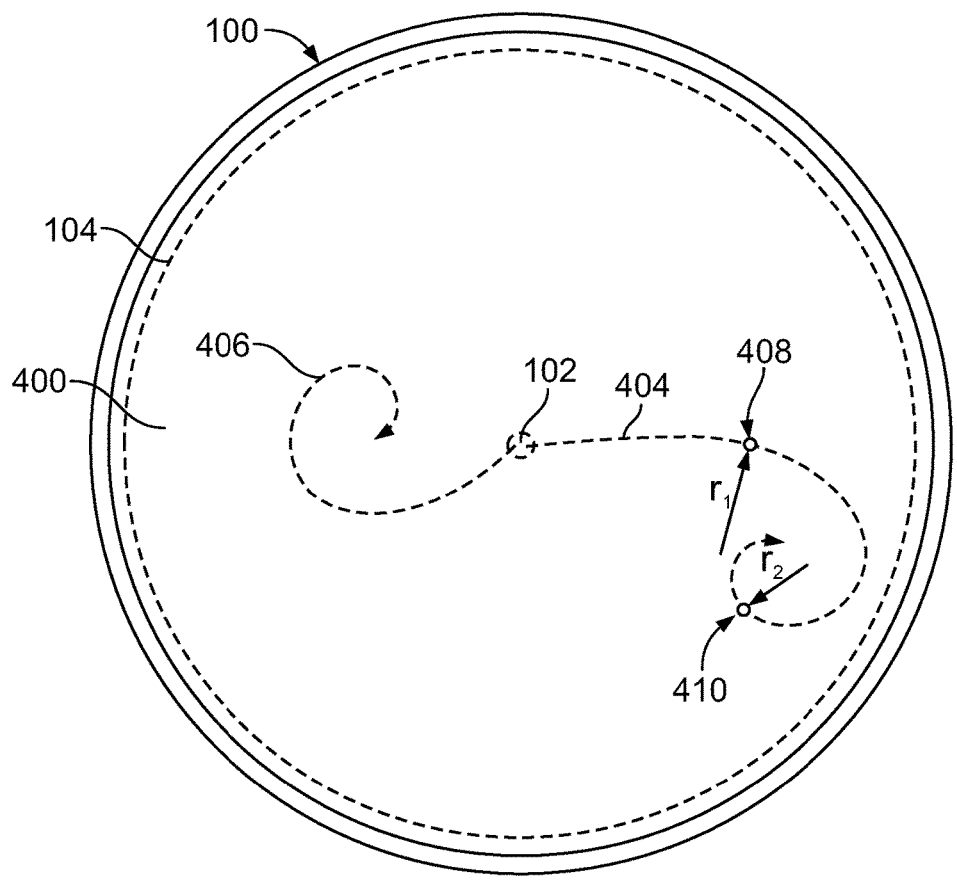
FIG. 6 illustrates a bottom view of an ionization chamber schematically showing curved paths of alpha particles, in accordance with an example implementation.

FIG. 5 illustrates a cross section of the ionization chamber 100 schematically showing curved paths of alpha particles, and FIG. 6 illustrates a bottom view of the ionization chamber 100 schematically showing curved paths of alpha particles, in accordance with an example implementation. Rather than traveling in the straight paths 110 and 112 toward the interior surface 114 or the electrodes 104, 106 as shown in FIG. 1, the alpha particles follow curved paths such as curved paths 404 and 406 as a result of the magnetic field 402.

Because an alpha particle traverses a curved path between two points rather than a straight line, the alpha particle travels a longer distance within the ionization chamber 100 due to the presence of the magnetic field 402. As a result of the curvature of the path traversed by an alpha particle, the alpha particle spends more time within the ionization chamber 100 and imparts more energy to the air molecules therein, thus ionizing more air molecules.

The extent of curvature of the curved path 404 or 406 at a particular point can be characterized by the magnitude of "curvature" at the particular point or by the radius of curvature, which is the inverse of "curvature." The radius of curvature at a particular point along the curved path 404 or 406 is estimated as the radius of a circular arc, which approximates the curved path at the particular point.

In an example, the radius "r" of curvature at a particular point of the curved path 404 or 406 (or any other curved path) traversed by an alpha particle can be determined using the following equation:

$$r = \frac{1}{B}\sqrt{\frac{2mV}{q}} \qquad (1)$$

where B is the magnetic field strength, m is the mass of the particle, V is the voltage applied to accelerate the alpha particle from a standstill to its present kinetic energy, and q is the charge of the alpha particle. As an example for illustration, if B is 1.2 Tesla (achievable with Neodymium rare-earth magnet), m is $6.62 \times 10^{-27}$ kilogram (mass of the alpha particle), V is $1.5 \times 10^6$ volts (voltage corresponding to kinetic energy of an alpha particle partly slowed from initially having 5 MeV energy and not yet slowed to the Bragg peak), then r can be calculated using equation (1) to be equal 0.21 meters.

The curvature of the paths 404 and 406 increases, and thus the radius of curvature decreases, as the alpha particle is slowed by air in the ionization chamber 100, i.e., as the alpha particle travels farther from the radioactive source 102. As an example for illustration, radius of curvature "$r_1$" of a point 408 along the curved path 404 is larger than a respective radius of curvature "$r_2$" of a point 410 that is traversed subsequent to traversal of the point 408 along the curved path 404 by an alpha particle. Because curvature is the inverse of the radius of curvature, then curvature at the point 410 is larger than curvature at the point 408. Thus, the farther the alpha particle travels along a particular path, the larger the path curvature, thereby giving the alpha particle more time within the ionization chamber 100 to impart energy to, and ionize, air molecules.

The magnetic field 402 may thus increase the amount of air that the alpha particle passes through as the alpha particle travels within the ionization chamber 100 from the radioactive source 102 toward the interior surface 114 or the electrodes 104, 106. If the alpha particle escapes the ionization chamber 100, the alpha particle would have created more ions therein compared to the configuration of FIG. 1.

Further, many alpha particles might not leave the ionization chamber 100. Rather, they may traverse a spiral path while still within the ionization chamber 100, thereby expending all their kinetic energy to create air ions. As such, the Bragg peak 304 shown in FIG. 3 occurs while the alpha particle is still within the ionization chamber 100, as opposed to just before or upon impacting the interior surface 114 or one of the electrodes 104, 106.

Due to the alpha particle spending more time traversing a curved path (e.g., the curved path 404 or 406) within the ionization chamber 100 and possibly stopping therein, an increased amount of energy of the alpha particle is spent ionization air molecules. The efficiency of the smoke detector 101, which could be measured as the amount of ionized air molecules for a given amount of radioactive material in the radioactive source 102, may thus increase. As a result of the increased efficiency, a smaller amount of radioactive material may be used to generate a given amount of ions within the ionization chamber 100.

Additionally, the size of the ionization chamber 100 may be decreased. In the configuration of FIG. 1 the alpha particle travels a certain straight line distance from the radioactive source 102 to the interior surface 114 of the ionization chamber 100 to ionize a given amount of air molecules. However, with the magnetic field 402 present, the alpha particle may require a smaller distance from the radioactive source 102 to the interior surface 114 of the ionization chamber 100 due to the curvature of the path it traverses to ionize the given mount of air molecules. Thus, the diameter or size of the ionization chamber 100 may be reduced, while maintaining the effectiveness and sensitivity of the smoke detector 101.

Referring back to FIG. 4, the magnetic field 402 is more effective when magnetic flux lines of the magnetic field 402 are substantially perpendicular to a plane of the electrodes 104 and 106. In other words, the magnetic field 402 is more effective when magnetic flux lines of the magnetic field 402 are substantially parallel to a longitudinal axis 412 of the ionization chamber 100. The term "substantially" is used herein to indicate that a flux line may form an angle with the longitudinal axis 412 that is less than a predetermined threshold angle, such as 30°.

The longitudinal axis 412 is a reference axis used herein to indicate an axis that is perpendicular to a plane of the electrodes 104, 106. For example, if the ionization chamber 100 is cylindrical and the electrodes 104, 106 are disposed at the respective bases of the ionization chamber 100, the longitudinal axis 412 is perpendicular to the bases of the ionization chamber 100. As another example, if the ionization chamber 100 is rectangular and the electrodes 104, 106 are disposed at opposing sides of the ionization chamber 100, the longitudinal axis 412 is perpendicular to the opposing sides at which the electrodes 104, 106 are disposed.

To render at least a portion of the magnetic flux lines substantially parallel to the longitudinal axis 412, the magnet 400 may be oriented as shown in FIG. 4 with the top side being magnetized as a north pole "N," and the bottom side being magnetized as a south pole "S." However, in other examples, the polarity could be reversed, with the top side being magnetized as a south pole "S," and the bottom side being magnetized as a north pole "N."

The angle that a magnetic flux line of the magnetic field 402 makes with the longitudinal axis 412 is non-uniform or inconsistent due its oval shape. For example, a magnetic flux line 414 may be oval-shaped, and therefore may form a smaller angle relative to the longitudinal axis 412 close to the electrode 106 of the ionization chamber 100. However, the angle of the magnetic flux line 414 relative to the longitudinal axis 412 increases where the magnetic flux line 414 is close to the interior surface 114 of the ionization chamber 100.

When the magnetic flux line 414 is substantially parallel to the longitudinal axis 412, the magnetic flux line 414 causes the alpha particle to curve laterally parallel to the plane of the electrodes 104 and 106 while it travels within the ionization chamber 100 away from the radioactive source 102. However, as the angle between the magnetic flux line 414 and the longitudinal axis 412 increases, e.g., the magnetic field 402 may cause the alpha particle to curve or deflect toward one of the electrodes 104 or 106. An alpha particle deflected toward the electrode 104 or 106 traverses a smaller distance before hitting the electrode, and therefore is less effective in ionizing air molecules. In an example, to render the magnetic flux lines of the magnetic field 402 more uniformly substantially parallel to the longitudinal axis 412, a second magnet may be used.

Figure 7:
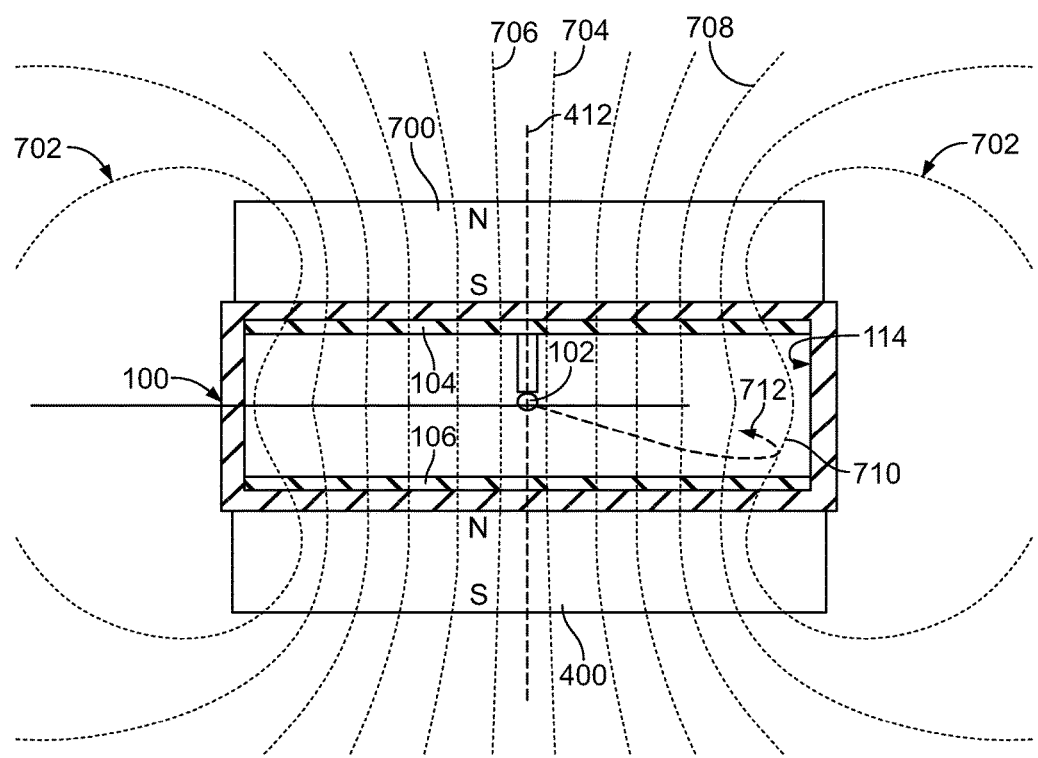
FIG. 7 illustrates two magnets coupled to an ionization chamber, in accordance with an example implementation.

FIG. 7 illustrates two magnets coupled to the ionization chamber 100, in accordance with an example implementation. As shown, in addition to the magnet 400, a second magnet 700 is coupled to the ionization chamber 100. In examples, the magnet 700 is coupled to an exterior surface of the ionization chamber 100 on an opposite side thereof relative to the magnet 400. For instance, the magnet 700 may be coupled to a side of the ionization chamber 100 that is adjacent to the electrode 104. The magnet 700 may be disposed parallel to the electrodes 104, 106 and the magnet 400.

In other examples, the magnet 700 may be mounted within the ionization chamber 100. In some examples, the magnet 700 might not be parallel to the electrodes 104, 106, or the magnet 400. The magnet 700 is disposed within the smoke detector 101, which is not shown in FIG. 7 to reduce visual clutter in the drawing.

In examples, the magnet 700 may be polarized as shown in FIG. 7 similar to the magnet 400. For example, if the top side of the magnet 400 is magnetized as a north pole "N," and its bottom side is magnetized as a south pole "S," then the top side of the magnet 700 is also magnetized as a north pole "N" and its bottom side is magnetized as a south pole "S." Alternatively, if the bottom side of the magnet 400 is magnetized as a north pole "N," and its top side is magnetized as a south pole "S," then the bottom side of the magnet 700 is also magnetized as a north pole "N" and its top side is magnetized as a south pole "S." With this configuration, the magnetic field 402 generated by the magnet 400 is reinforced by the respective magnetic field generated by the magnet 700.

The magnets 400 and 700 cooperate to generate a magnetic field 702 having magnetic flux lines passing through the air within the ionization chamber 100. Alignment or degree of parallelism of magnetic flux lines of the magnetic field 702 relative to the longitudinal axis 412 of the ionization chamber 100 is enhanced compared to the configuration of FIG. 4, where one magnet is used.

For example, magnetic flux lines 704 and 706 are substantially parallel to the longitudinal axis 412, e.g., the flux lines 704 and 706 may form an angle with the longitudinal axis 412 that is less than a predetermined threshold angle, such as 5°. Even peripheral magnetic flux lines located away from the longitudinal axis 412 and closer to a periphery of the longitudinal chamber 100 such as magnetic flux line 708, are substantially parallel to the axis 412. As such, the configuration of FIG. 7 may be more effective in ionizing air molecules within the ionization chamber 100.

Further, magnetic flux lines that are located close to the periphery or rim of the ionization chamber 100, such as magnetic flux line 710, have concave portions near the interior surface 114 as shown in FIG. 7. These concave portions may help deflect alpha particles away from both electrodes 104 and 106. Such deflection is shown schematically by curved path 712 in FIG. 7 indicating that the alpha particle reaching a curved portion of the flux line 710 deflects away from the electrode 106 back toward the inner space of the ionization chamber 100. This way, the alpha particle spends more of its life-time within the ionization chamber 100 ionizing air molecules and enhancing the efficiency of the smoke detector 101.

In examples, the magnets 400, 700 may be permanent magnets. For instance, the magnets 400, 700 may include samarium-cobalt magnets, which is a type of rare-earth permanent magnets made of an alloy of samarium and cobalt. Alternatively, the magnets 400, 700 may include neodymium magnets (also known as NdFeB, NIB, or Neo magnet), which is a type of rare-earth permanent magnets made from an alloy of neodymium, iron and boron. Other types of permanent magnets could be used.

In another example, the magnets 400, 700 could be electro-magnets, where the magnetic field 402 or 702 is produced by an electric current. In this example, the magnets 400, 700 may include an insulated wire wound into a coil. A current through the wire creates a magnetic field, which is concentrated in the hole at the center of the coil. The wire may be wound around a magnetic core made from a ferromagnetic or ferrimagnetic material such as iron to concentrate the magnetic flux.

In another example, the magnets 400, 700 could be electro-permanent magnets (EPMs). An EPM is a type of magnet that includes both an electromagnet and a dual material permanent magnet. A magnetic field produced by the electro-magnet is used to change the magnetization of the permanent magnet. In an example, the permanent magnet includes magnetically soft and hard materials, where the soft material has lower magnetic coercivity compared to the hard material and can thus have its magnetization changed. When the magnetically soft and hard materials have opposite magnetizations, the EPM has no net magnetic field, and when they are aligned, the EPM generates an external magnetic field.

In examples, the magnets 400, 700 could be made of the same type of magnets. In other examples, the magnet 400 could be made of a different magnet type than the magnet 700.

In some cases, magnets could be costly. In order to reduce cost, a single magnet (e.g., the magnet 400 or 700) could be used along with a member made of a ferromagnetic or ferrimagnetic material such as iron to concentrate the magnetic flux in the ionization chamber 100.

Figure 8:
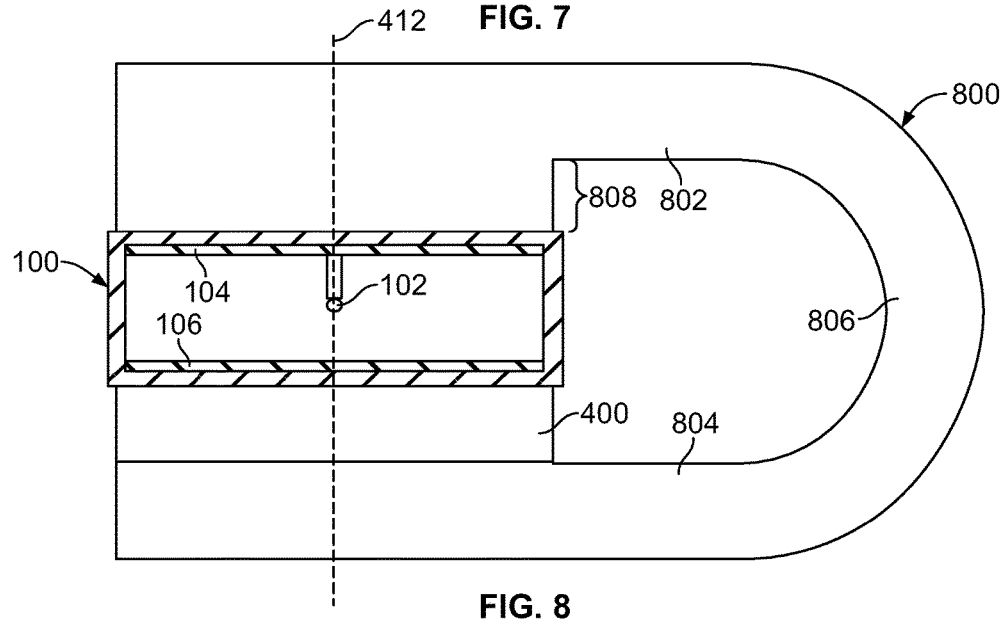
FIG. 8 illustrates using a single magnet with a yoke to enhance a magnetic field generated within an ionization chamber, in accordance with an example implementation.

FIG. 8 illustrates using the magnet 400 with a yoke 800 to enhance a magnetic field generated within the ionization chamber 100, in accordance with an example implementation. In an example, the yoke 800 is generally U-shaped and has two generally parallel and laterally disposed leg portions 802 and 804 and a connecting portion 806 that couples or connects the leg portions 802 and 804 to each other.

As shown in FIG. 8, the leg portion 804 interfaces, directly or indirectly, with the magnet 400. In examples, the leg portion 804 presses against the magnet 400. The magnetic field generated by the magnet 400 is carried or transmitted via the leg portion 804, through the connecting portion 806 and the leg portion 802, to the other side of the ionization chamber 100 adjacent to the electrode 104.

The yoke 800 may be made of high-permeability ferromagnetic or ferrimagnetic material that reduces magnetic reluctance, thus increasing strength of and concentrating the magnetic flux generated by the magnet 400. The yoke 800 further operates as a channel that transfers the magnetic field to the other side of the ionization chamber 100, thereby operating as a second magnet disposed on the other side of the ionization chamber 100 adjacent to the electrode 104. Thus, the yoke 800 may be used in lieu of the magnet 700, and cost may thus be reduced.

Further, the yoke 800, and specifically the leg portion 802, may include a protrusion 808 shaped similar to the magnet 700. The protrusion 808 may enhance alignment or degree of parallelism of the magnetic flux lines within the ionization chamber 100 relative to the longitudinal axis 412.

Although FIG. 8 illustrates using the yoke 800 with the magnet 400, the yoke 800 could be configured to be used with the magnet 700 disposed adjacent to the electrode 104 as shown in FIG. 7. In another example, the yoke 800 could be used with the configuration of FIG. 7 with the two magnets 400 to 700 to further enhance the magnetic field. Further, the yoke 800 can be referred to as a coupling member and may assume other geometrical shapes than a U-shaped yoke, e.g., a cylindrical or other shape.

The detailed description above describes various features and operations of the disclosed systems with reference to the accompanying figures. The illustrative implementations described herein are not meant to be limiting. Certain aspects of the disclosed systems can be arranged and combined in a wide variety of different configurations, all of which are contemplated herein.

Further, unless context suggests otherwise, the features illustrated in each of the figures may be used in combination with one another. Thus, the figures should be generally viewed as component aspects of one or more overall implementations, with the understanding that not all illustrated features are necessary for each implementation.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

Further, devices or systems may be used or configured to perform functions presented in the figures. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner.

By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide The arrangements described herein are for purposes of example only. As such, those skilled in the art will appreciate that other arrangements and other elements (e.g., machines, interfaces, operations, orders, and groupings of operations, etc.) can be used instead, and some elements may be omitted altogether according to the desired results. Further, many of the elements that are described are functional entities that may be implemented as discrete or distributed components or in conjunction with other components, in any suitable combination and location.

While various aspects and implementations have been disclosed herein, other aspects and implementations will be apparent to those skilled in the art. The various aspects and implementations disclosed herein are for purposes of illustration and are not intended to be limiting, with the true scope being indicated by the following claims, along with the full scope of equivalents to which such claims are entitled. Also, the terminology used herein is for the purpose of describing particular implementations only, and is not intended to be limiting.

What is claimed is:

1. A smoke detector comprising:
a chamber;
a first electrode disposed within the chamber;
a second electrode disposed within the chamber, wherein gas is disposed in an inner space of the chamber between the first electrode and the second electrode;
a radioactive source generating alpha particles within inner space of the chamber; and
a magnet disposed in the smoke detector and coupled to the chamber, wherein the magnet generates a magnetic field in the inner space of the chamber.

2. The smoke detector of claim 1, wherein the chamber is shaped as a cylinder, wherein the first electrode is disposed within the cylinder at a first base thereof, and wherein the second electrode is disposed within the cylinder at a second base thereof opposite the first base.

3. The smoke detector of claim 1, wherein the magnet is coupled to an exterior surface of the chamber adjacent to the first electrode or the second electrode.

4. The smoke detector of claim 1, further comprising:
a pole coupled to the first electrode or the second electrode, wherein the pole protrudes within the inner space of the chamber, and wherein the radioactive source is coupled to the pole.

5. The smoke detector of claim 1, wherein the magnet is a first magnet mounted to a first side of the chamber, and wherein the smoke detector further comprises:
a second magnet mounted to a second side of the chamber opposite the first side thereof.

6. The smoke detector of claim 1, wherein the magnet is mounted to a first side of the chamber, and wherein the smoke detector further comprises:
a coupling member coupled to the magnet mounted to the first side of the chamber, wherein the coupling member interfaces with a second side of the chamber opposite the first side thereof.

7. The smoke detector of claim 6, wherein the coupling member includes a yoke having a U-shape and comprising: (i) a first leg portion coupled to the magnet, (ii) a second leg portion coupled to the second side of the chamber, and (iii) a connecting portion that couples the first leg portion to the second leg portion.

8. The smoke detector of claim 6, wherein the coupling member is made of a ferromagnetic or ferrimagnetic material.

9. The smoke detector of claim 1, wherein the magnet includes a permanent magnet, an electro-magnet, or an electro-permanent magnet.

10. A smoke detector comprising:
a chamber;
a first electrode disposed within the chamber;
a second electrode disposed within the chamber, wherein air is disposed within the chamber between the first electrode and the second electrode;
a radioactive source emitting alpha particles in the air between the first electrode and the second electrode; and
a magnet disposed in the smoke detector and coupled to the chamber, wherein the magnet generates a magnetic field having magnetic flux lines passing through the air between the first electrode and the second electrode, and wherein the magnet is oriented such that at least a portion of the magnetic flux lines is substantially parallel to a longitudinal axis of the chamber.

11. The smoke detector of claim 10, wherein the chamber is shaped as a cylinder, wherein the first electrode is disposed within the cylinder at a first base thereof, and wherein the second electrode is disposed within the cylinder at a second base thereof opposite the first base.

12. The smoke detector of claim 10, wherein the magnet is coupled to an exterior surface of the chamber adjacent to the first electrode or the second electrode.

13. The smoke detector of claim 10, further comprising:
a pole coupled to the first electrode or the second electrode, wherein the pole protrudes within the inner space of the chamber, and wherein the radioactive source is coupled to a tip of the pole.

14. The smoke detector of claim 10, wherein the magnet is a first magnet mounted to a first side of the chamber, and wherein the smoke detector further comprises:

a second magnet mounted to a second side of the chamber opposite the first side thereof.

15. The smoke detector of claim 10, wherein the magnet is mounted to a first side of the chamber, and wherein the smoke detector further comprises:
a yoke that is U-shaped and comprising: (i) a first leg portion coupled to the magnet, (ii) a second leg portion coupled to a second side of the chamber opposite the first side thereof, and (iii) a connecting portion that couples the first leg portion to the second leg portion.

16. A smoke detector comprising:
a chamber;
a first electrode disposed within the chamber;
a second electrode disposed within the chamber, wherein air is disposed between the first electrode and the second electrode;
a radioactive source emitting alpha particles in the air between the first electrode and the second electrode;
a first magnet mounted to an exterior surface of the chamber at a first side of the chamber; and
a second magnet mounted to the exterior surface of the chamber at a second side of the chamber opposite the first side thereof, wherein the first magnet and the second magnet cooperate to generate a magnetic field having magnetic flux lines passing through the air disposed between the first electrode and the second electrode.

17. The smoke detector of claim 16, wherein the chamber is shaped as a cylinder, wherein the first electrode is disposed within the cylinder at a first base thereof, and wherein the second electrode is disposed within the cylinder at a second base thereof opposite the first base.

18. The smoke detector of claim 16, wherein the first electrode is coupled to an interior surface of the chamber at the first side adjacent to the first magnet, and wherein the second electrode is coupled to the interior surface of the chamber at the second side adjacent to the second magnet.

19. The smoke detector of claim 16, wherein the first and second magnets are oriented such that at least a portion of the magnetic flux lines is substantially parallel to a longitudinal axis of the chamber.

20. The smoke detector of claim 16, further comprising:
a pole coupled to the first electrode or the second electrode, wherein the pole protrudes within the inner space of the chamber, and wherein the radioactive source is coupled to a tip of the pole such that the radioactive source is positioned proximate to a center of the chamber.

* * * * *